US009354206B2

(12) United States Patent
Zalameda et al.

(10) Patent No.: US 9,354,206 B2
(45) Date of Patent: May 31, 2016

(54) FLOATING ULTRASONIC TRANSDUCER INSPECTION SYSTEM AND METHOD FOR NONDESTRUCTIVE EVALUATION

(75) Inventors: Joseph N. Zalameda, Poquoson, VA (US); Patrick H. Johnston, Newport News, VA (US)

(73) Assignee: THE UNITED STATES OF AMERICA AS REPRESENTED BY THE ADMINISTRATOR OF THE NATIONAL AERONAUTICS AND SPACE ADMINISTRATION, Washington, DC (US)

( * ) Notice: Subject to any disclaimer, the term of this patent is extended or adjusted under 35 U.S.C. 154(b) by 900 days.

(21) Appl. No.: 13/557,250

(22) Filed: Jul. 25, 2012

(65) Prior Publication Data

US 2013/0030727 A1 Jan. 31, 2013

Related U.S. Application Data

(60) Provisional application No. 61/511,182, filed on Jul. 25, 2011.

(51) Int. Cl.
| G01N 29/11 | (2006.01) |
| G01N 29/04 | (2006.01) |
| G01N 29/265 | (2006.01) |
| G01N 29/28 | (2006.01) |
| G01N 29/44 | (2006.01) |

(52) U.S. Cl.
CPC .............. *G01N 29/11* (2013.01); *G01N 29/045* (2013.01); *G01N 29/265* (2013.01); *G01N 29/28* (2013.01); *G01N 29/4436* (2013.01)

(58) Field of Classification Search
CPC .............. G01N 29/045; G01N 29/343; G01N 29/2437; G01N 29/044
See application file for complete search history.

(56) References Cited

U.S. PATENT DOCUMENTS

| 4,020,679 | A | * | 5/1977 | Barry .............................. 73/644 |
| 4,068,523 | A | * | 1/1978 | Hetherington et al. ......... 73/628 |
| 4,545,251 | A | * | 10/1985 | Uchida et al. ................... 73/631 |
| 5,469,744 | A | | 11/1995 | Patton et al. |
| 6,004,272 | A | * | 12/1999 | Barry .................. A61B 8/0875 600/449 |

(Continued)

OTHER PUBLICATIONS

Gardner, C. G., "Nondestructive Testing", 1973, Published by NASA Technology Utilization Office, pp. 40-41.*

(Continued)

*Primary Examiner* — Alexander Satanovsky
(74) *Attorney, Agent, or Firm* — Andrea Z. Warmbier (57) ABSTRACT

A method for inspecting a structural sample using ultrasonic energy includes positioning an ultrasonic transducer adjacent to a surface of the sample, and then transmitting ultrasonic energy into the sample. Force pulses are applied to the transducer concurrently with transmission of the ultrasonic energy. A host machine processes ultrasonic return pulses from an ultrasonic pulser/receiver to quantify attenuation of the ultrasonic energy within the sample. The host machine detects a defect in the sample using the quantified level of attenuation. The method may include positioning a dry couplant between an ultrasonic transducer and the surface. A system includes an actuator, an ultrasonic transducer, a dry couplant between the transducer the sample, a scanning device that moves the actuator and transducer, and a measurement system having a pulsed actuator power supply, an ultrasonic pulser/receiver, and a host machine that executes the above method.

17 Claims, 5 Drawing Sheets

(56) References Cited

U.S. PATENT DOCUMENTS

| | | | | |
|---|---|---|---|---|
| 6,301,967 | B1* | 10/2001 | Donskoy et al. | 73/579 |
| 7,387,612 | B2* | 6/2008 | Pal et al. | 601/2 |
| 7,926,344 | B1* | 4/2011 | Hyde | G01F 23/2968 73/290 B |
| 8,087,298 | B1* | 1/2012 | DiMambro et al. | 73/629 |
| 2008/0282805 | A1* | 11/2008 | Onodera et al. | 73/629 |
| 2011/0162455 | A1* | 7/2011 | Renzel | G01N 29/343 73/632 |

OTHER PUBLICATIONS

Scherge, M. and Gorb, S., "Biological Micro- and Nano-tribology", 2001, Published by Springer, pp. 70-73.*

Geere, D., "Vacuum-powered Robot Climbs up Walls", Jul. 2, 2010, Published by Wired, p. 3.*

ASTM E494—Standard Practice for Measuring Ultrasonic Velocity in Materials, Website, http://www.astm.org/Standards/E494.htm, Copyright 1996-2012, pp. 1-3.

Qualitest, Inc.—Ultrasonic Crawler System—Scanmap VS. Website, http://www.qualitest-inc.com/scanmap.htm, Copyright 1999-2012, pp. 1-2.

The Dripless Bubbler Ultrasonic Scanner and its Utilities in Aircraft NDI, Website, http://www.ndt.net/abstract/asntf97/032.htm, Copyright Dec. 1, 1997, p. 1.

QMI—The New* Sonda-007CX, Website, http://www.qmi-inc.com/sonda.htm, last accessed on Dec. 3, 2012, pp. 1-2.

Sonatest Array WheelProbe, Website, http://www.sonatest.com/products/range/automated-ut/wheelprobe/array/, Copyright 2012, pp. 1-2.

* cited by examiner

FLOATING ULTRASONIC TRANSDUCER INSPECTION SYSTEM AND METHOD FOR NONDESTRUCTIVE EVALUATION

CROSS-REFERENCE TO RELATED APPLICATION

This application claims the benefit of and priority to U.S. Provisional Patent Application No. 61/511,182 filed on Jul. 25, 2011, which is hereby incorporated by reference in its entirety.

STATEMENT REGARDING FEDERALLY SPONSORED RESEARCH OR DEVELOPMENT

The invention described herein was made by employees of the United States Government, and may be manufactured and used by or for the Government for Government purposes without the payment of any royalties thereon or therefor.

TECHNICAL FIELD

The present disclosure relates to an ultrasonic inspection system having a floating ultrasonic transducer for use in the nondestructive inspection and evaluation of a structural sample.

BACKGROUND OF THE INVENTION

Ultrasonic scanning is a nondestructive inspection and evaluation technique that is used to determine the structural integrity of a sample such as an aircraft fuselage skin or another metal/composite structural sample. In a typical ultrasonic scanning device, ultrasonic energy is directed into a sample while a computer device measures the attenuation of ultrasonic energy waves as the waves propagate through the sample. Waveform attenuation is affected by defects in the sample such as hairline fractures, voids, delamination, and corrosion. Such defects may be all but imperceptible to the human eye, and can thus escape detection absent the use of more sophisticated interrogation techniques. As a result, ultrasonic scanning may be used to inspect structural samples and thereby determine structural integrity. However, conventional ultrasonic scanning systems may be less than optimal when used with certain types of structural samples.

SUMMARY OF THE INVENTION

A method is disclosed herein for ultrasonically inspecting a structural sample. The disclosed method does not require water, gel, or any other wet coupling medium at the surface of the sample that is being inspected. In the present approach, a controlled vertical displacement is applied via a train of force pulses transmitted to an ultrasonic transducer in conjunction with a transmission of ultrasonic energy. The intermittent contact that results between the transducer and the inspected surface allows the transducer to glide, hop, or otherwise "float" with respect to the surface. The present approach reduces the average applied force to the interrogated surface, which, when multiplied by the coefficient of friction of the surface, gives a reduced net frictional force resisting the motion of the transducer. As a result, the transducer can be more easily moved with respect to the surface.

The overall reduction in net frictional force at the surface is determined relative to other approaches, for instance that of rolling transducers which require a straight, one-dimensional roll path. Such approaches may be less than optimal for quickly scanning the structure in a free form manner. Another common inspection approach is the dripless bubble system, which allows water to flow onto the surface of the interrogated sample. Alternatively, the entire sample may be submersed in a water tank. Leakage, the potential for air bubbles, and incompatibility of water with some carbon composite materials may make dripless/submersible scanning devices less than optimal in certain applications. For example, the exposed surfaces of an aircraft fuselage or a space vehicle may be such that moisture and other surface contamination must be avoided.

In particular, a method is disclosed herein for inspecting a structural sample using ultrasonic energy. The method includes positioning an ultrasonic transducer adjacent to a surface of the sample, and then transmitting ultrasonic energy into the sample as ultrasonic pulses. The method also includes applying vertical displacement to the transducer via a train of force pulses, e.g., at a sonic frequency, transmitted concurrently with transmission of the ultrasonic energy. The pulses vertically displace the transducer and cause the transducer to exert a periodic force on the surface. The transducer floats with respect to the surface between consecutive force pulses. The method additionally includes processing an ultrasonic return pulse using a host machine to quantify a level of attenuation of the ultrasonic energy within the sample, and then using the host machine to detect a defect in the sample using the quantified level of attenuation.

A system for inspecting a structural sample using ultrasonic energy includes an ultrasonic transducer connected to an actuator, dry couplant, and a measurement system. The dry couplant is positioned between the ultrasonic transducer and a surface of the structural sample. The measurement system includes a pulsed actuator power supply, an ultrasonic pulser/receiver, and a host machine having a processor and a tangible, non-transitory memory device(s). A set of instructions for inspecting the sample is recorded in the memory device. The scanning device, and/or a separate positioning device, moves the actuator and transducer with respect to the surface during inspection of the sample.

Execution of the instructions by the processor causes the ultrasonic puller/receiver to transmit ultrasonic energy into the sample via the transducer, and causes the power supply to vertically displace the transducer, via the actuator, concurrently with transmission of the ultrasonic input pulses. The displacement causes the transducer to exert a periodic force on the surface. The processor then processes an ultrasonic return pulse from the ultrasonic pulser/receiver to quantify a level of attenuation of the ultrasonic input pulses within the sample. The host machine detects a defect in the sample using the quantified level of attenuation.

Another method for inspecting a structural sample using ultrasonic energy includes positioning a dry couplant in the form of a flexible membrane between an ultrasonic transducer and a surface of the sample, and then using an actuator to cause the transducer to exert a periodic force on the surface of the structural sample. The periodic force in one embodiment has a sonic frequency of at least 50 Hz. The method also includes transmitting ultrasonic energy at an ultrasonic frequency of in an example embodiment, at least 1 MHz into the structural sample using the transducer and an ultrasonic pulser/receiver, synchronizing the transmission of pulses of the ultrasonic energy with the periodic force while moving the transducer with respect to the surface, and processing ultrasonic return pulses from the sample using a host machine to quantify a level of attenuation of the ultrasonic energy within the sample. The method further includes using the host machine to detect a defect in the sample as a function of the level of attenuation.

The above features and advantages and other features and advantages of the present invention are readily apparent from the following detailed description of the best modes for carrying out the invention when taken in connection with the accompanying drawings.

DETAILED DESCRIPTION OF THE INVENTION

Referring to the drawings, and beginning with FIG. 1, an ultrasonic interrogation and inspection system 10 is disclosed herein that uses an ultrasonic transducer 12 in conjunction with a dry coupling medium, hereinafter referred to as dry couplant 20, to perform a nondestructive ultrasonic evaluation of a structural sample 14. The system 10 reduces the effects of surface friction with respect to an inspected surface 13 of the sample 14 by establishing intermittent/pulsed contact between the transducer 12 and the surface 13, typically at a sonic frequency, and by concurrently conducting ultrasonic sampling at a higher frequency. This synchronized, dual-frequency sampling approach allows the transducer 12 to "float" with respect to the surface 13, i.e., to hop, glide, or otherwise move across the surface 13 between force pulses with a much reduced or zero contact force. At the same time, adequate dry coupling is provided via the dry couplant 20 between the transducer 12 and the sample 14 for optimal ultrasonic measurement.

Figure 1:
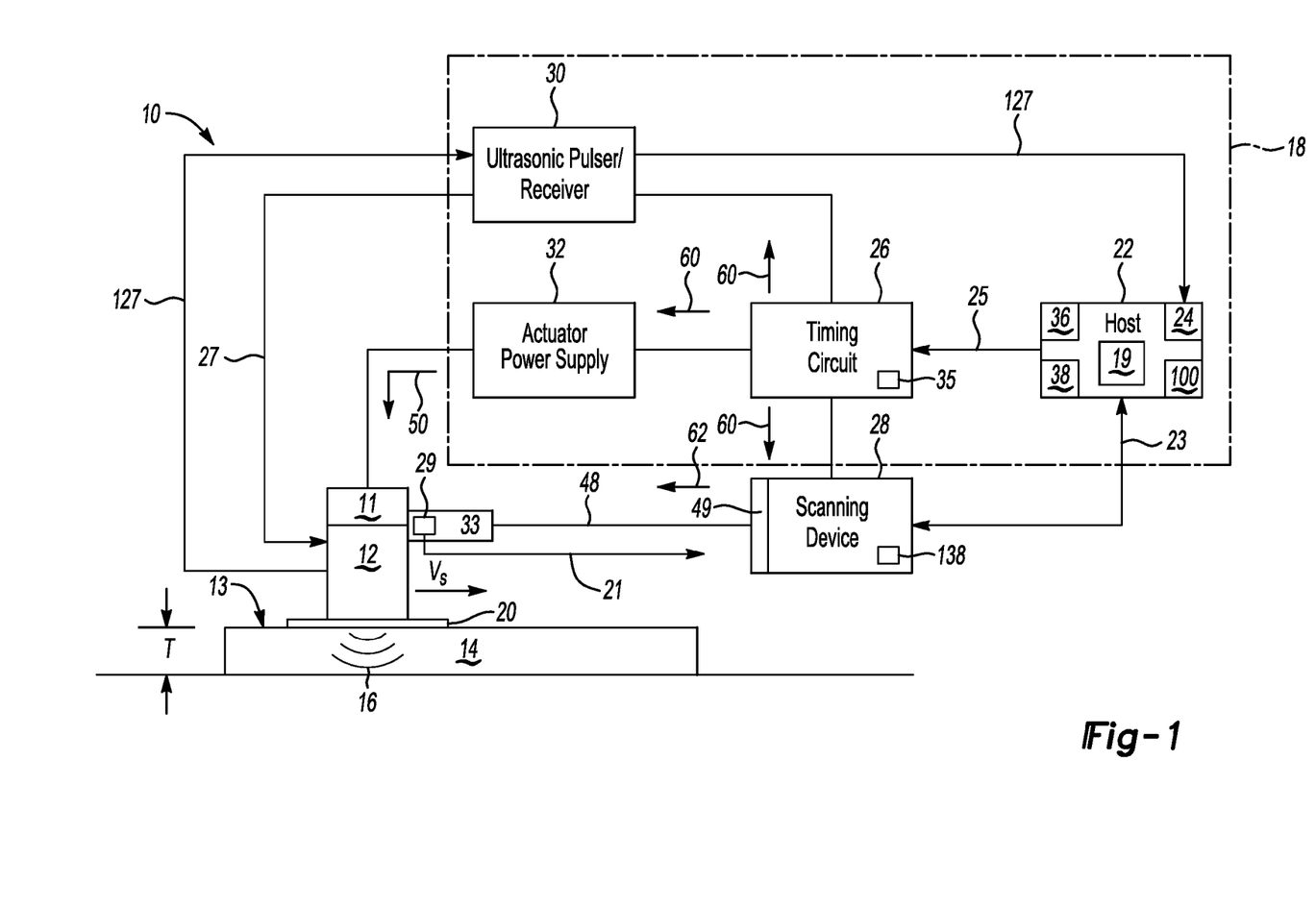
FIG. 1 is a schematic illustration of a floating ultrasonic transducer system used for nondestructive inspection and evaluation of a structural sample as set forth herein.

The sample 14 shown in FIG. 1 has a thickness T, and may be constructed of a single metal such as aluminum and/or of composite materials or alloys of metal. In an example application, the sample 14 may be embodied as a skin of a fuselage or any other structural element in which surface contamination and/or post-inspection surface cleaning is undesirable.

The system 10 includes an actuator 11 such as a linear voice coil motor or piezoelectric stack, the ultrasonic transducer 12, a scanning device 28, and a measurement system 18, each of which is described in turn below. The transducer 12 interrogates the sample 14 by directing waves 16 of ultrasonic into the sample 14 as ultrasonic input pulses. As well understood in the art, a transducer such as the transducer 12 disclosed herein converts an electrical signal into a mechanical vibration and vice versa. The transducer 12 may contain a piezoelectric element, crystal, or other suitable device for this purpose. The ultrasonic transducer 12 shown in FIG. 1 may be configured as a single transducer 12 or as an array of similarly configured transducers 12, with the latter configuration being well suited for achieving multiple inspections at a single contact point. In all embodiments, the transducer 12 vibrates at ultrasonic frequencies, which may be frequencies higher than about 20 kHz. In some embodiments the transducer generates the waves 16 at much higher frequencies, e.g., of over 1 MHz or over 25 MHz in different example embodiments. In other embodiments, such as when inspecting a relatively thick sample such as tank armor, lower frequencies on the order of hundreds of KHz may be used.

Additionally, the actuator 11 applies a train of force pulses, hereinafter referred to as sonic pulses, to the transducer 12 to cause intermittent/tapping contact between the transducer 12 and the surface 13. While the force pulses may be applied at an ultrasonic frequency in other embodiments, in all embodiments the applied frequency should be lower than the ultrasonic frequency used for ultrasonic scanning. For illustrative consistency, the term "sonic pulses" will be used hereinafter.

In a particular embodiment, a pulse frequency of about 50-70 Hz may be used concurrently with transmission of the ultrasonic waves 16. An example sonic/ultrasonic frequency pairing includes sonic pulses of about 63 Hz synchronized with transmission of the ultrasonic waves 16 at a frequency of about 35 MHz to 40 MHz, i.e., ±5%, an embodiment which works particularly well with a sample 14 in the form of a graphite/epoxy composite plate. The actual sonic/ultrasonic frequency combination may be expected to vary with the composition and thickness of the sample 14.

Still referring to FIG. 1, the transducer 12 is coupled to the surface 13 using the dry couplant 20. While a gel, water, or any other wet couplant may be used between the transducer 12 and the dry couplant 20 to minimize impedance losses, any interface between the dry couplant 20 and the surface 13 always remains dry in the present approach. This condition eliminates the need for post-inspection cleaning of the surface 13. The ultrasonic transducer 12 of FIG. 1 acts in conjunction with the dry couplant 20 to achieve the momentary/intermittent touching control approach as set forth herein. The dry couplant 20 couples the transmitted ultrasonic waves 16 emanating from the transducer 12 with the material of the sample 14.

By way of example, the dry couplant 20 may be variously embodied as a low-attenuation dry elastomer such as nitrile or another synthetic rubber, a liquid-filled thin membrane, or a hydrophilic material. In the configuration shown in FIG. 1, the dry couplant 20 is a membrane positioned over the surface 13, and thus remains stationary with respect to the moving transducer 12. In other embodiments a membrane sock may be positioned over the transducer 12 to allow the dry couplant 20 to move with the transducer 12.

Figure 1A:
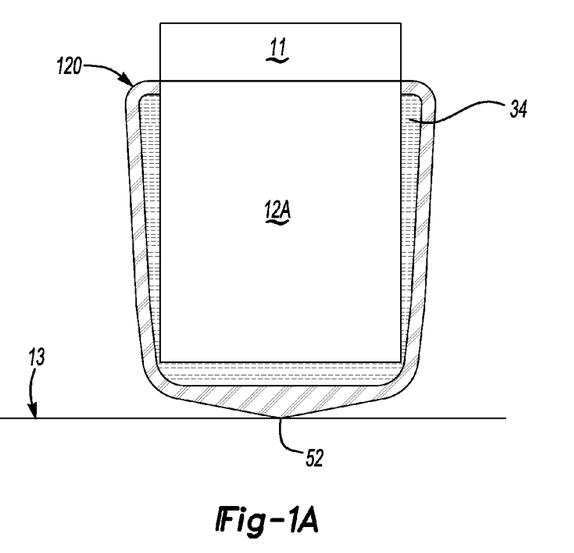
FIG. 1A is a schematic illustration of an optional encapsulated transducer that is usable as part of the system shown in FIG. 1.

Referring briefly to FIG. 1A, an alternative transducer 12A may be encapsulated by an alternative dry couplant 120. For example, the dry couplant 120 may define a volume of fluid 34 such as water or gel. The dry couplant 120 may be shaped as a capsule that fully encloses the transducer 12A and the fluid 34 therein. A flexible tip 52 may transmit the sonic pulses as intermittent forces to the surface 13 when the transducer 12A is activated by the actuator 11 without damaging the dry couplant 20.

Referring again to FIG. 1, the scanning device 28 includes a processor 138 and a positioning device 33, which is connected via an arm 48 to a stationary member 49. The positioning device 33 may be embodied as a set of motors or rotary/linear actuators that position the transducer 12 in both the horizontal and vertical directions as needed. A position sensor 29 may be connected to the positioning device 33 or the transducer 12 and used to measure the relative position of the transducer 12. The measured position (arrow 21) may be transmitted to a processor 138 of the scanning device 28. The scanning system 28 then outputs a position control signal (arrow 62) to the positioning device 33 to control the positioning of the actuator 11 and transducer 12 in a control loop, thereby using the measured position (arrow 21) as a feedback signal.

The measurement system 18 includes a host machine 22, a timing circuit 26, an ultrasonic pulser/receiver 30 in communication with the transducer 12, and an actuator power supply 32. The host machine 22 of FIG. 1 includes all necessary software and hardware necessary for conducting the present method 100, an example of which is described below with reference to FIG. 6. The host machine 22 may include a display 19 and a digitizer 24, as well as tangible, non-transitory memory device 36 on which is recorded computer-executable code embodying the present method 100. A bus (double arrow 23) may connect the host machine 22 to the scanning device 28.

The host machine 22 also includes a processor 38 and any required data busses. Memory device 36 may include read only memory (ROM), electrically-programmable read-only memory (EPROM), flash memory, or any other non-transitory, computer readable media. Such memory is relatively permanent, and thus may be used to retain values needed for later access by the processor 38. The host machine 22 may also include sufficient transitory memory, e.g., random access memory (RAM). Such memory may include the values of any transient signals communicated within the system 10 in conducting the present method 100.

The host machine 22 transmits a scan request (arrow 25) to the timing circuit 26 to initiate sampling. The scan request (arrow 25) may include all required scanning parameters, such as the frequency and amplitude of the sonic pulses to the actuator 11, the ultrasonic scanning frequency of the waves 16, etc. The timing circuit 26 receives the scan request (arrow 25) and using a logic block 35, generates and transmits synchronized output signals (arrows 60) to each of the ultrasonic puller/receiver 30, actuator power supply 32, and scanning device 28.

The pulser/receiver 30 may be embodied as an electronics box, e.g., an Olympus Panametrics 5072PR or similar device, that produces the ultrasonic input pulses (arrow 27) and transmits the same to the transducer 12, and also measures, receives, filters, and amplifies the ultrasonic return pulses (arrow 127) returned from the transducer 12. The received and processed return pulses (arrow 127) are then fed to the digitizer 24 within the host machine 22. The ultrasonic input pulses (arrow 27) from the ultrasonic pulser/receiver 30 are synchronized with the sonic pulses generated by a pulsed output signal (arrow 50) from the actuator power supply 32. The ultrasonic pulser/receiver 30 then reads and relays the ultrasonic return pulses (arrow 127) back to the host machine 22, where the digitizer 24 converts the received return pulse (arrow 127) as needed into a form usable for processing and display of results.

Figure 1B:
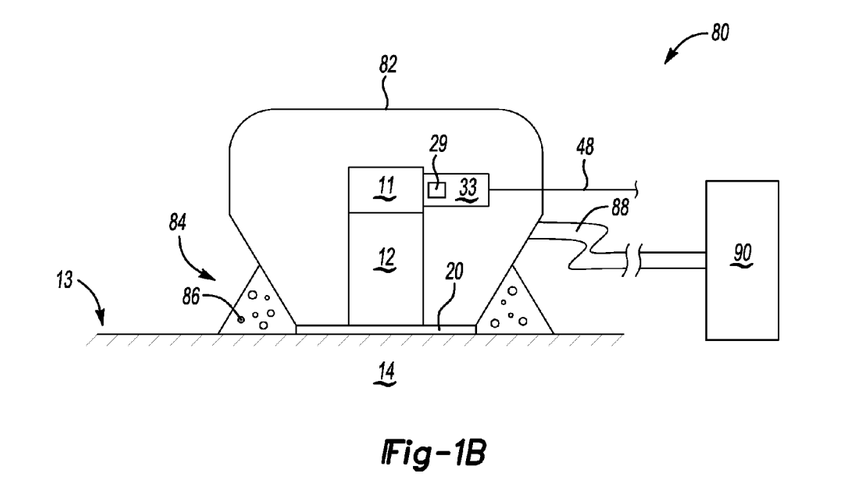
FIG. 1B is a schematic illustration of an optional vacuum-assisted transducer that is usable as part of the system shown in FIG. 1.

Referring to FIG. 1B, in an alternative embodiment, a handheld subsystem 80 may include the actuator 11, the transducer 12, and the dry couplant 20, all of which may be enclosed or encapsulated within a housing 82. For illustrative simplicity, the housing 82 is shown schematically. Various configurations may suffice, such as metal, plastic, composite, etc. The housing 82 may include a perforated skirt 84, i.e., defining pores 86. The pores 86 are in fluid communication with the interior of the housing 82, and are present on all surfaces of the skirt 84, including adjacent to the surface 13. A vacuum tube 88 may extend from the housing 82 to a vacuum source 90 such as a pump. Thus, vacuum applied by the vacuum source 90 may reach the surface 13 via the housing 82 and the pores 86.

In this example embodiment, suction force may be applied to the housing 82 to offset the periodic tapping force needed to couple the ultrasonic energy from the transducer 12 into the sample 14. Such a suction force should be minimal to allow the housing 82, which may define part of a handheld scanning module, to float with respect to the surface 13 during scanning. Such an embodiment may be advantageous when used to inspect vertical or overhead surfaces.

Figure 2:
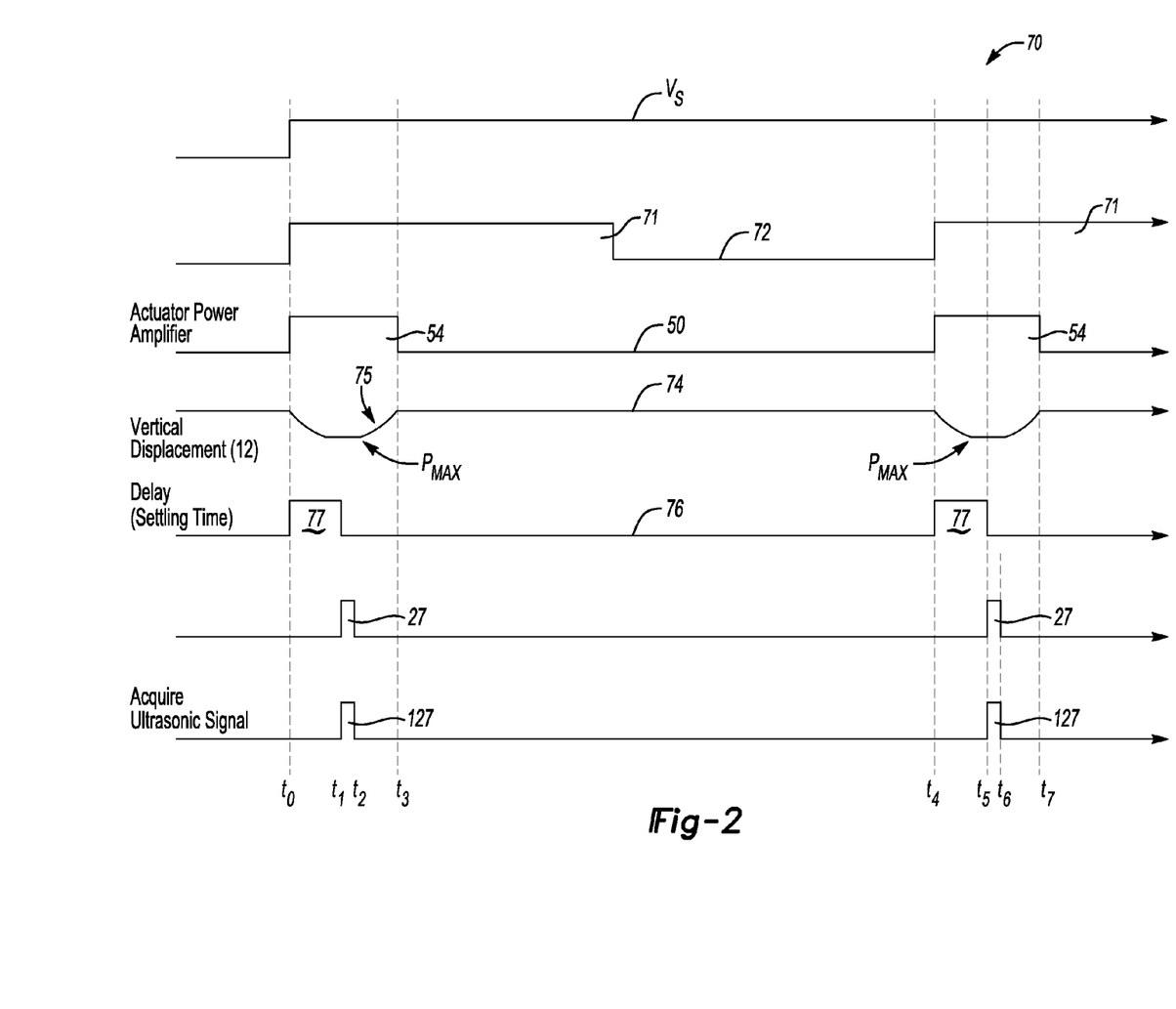
FIG. 2 is an example set of traces that collectively describes the operation of the system shown in FIG. 1.

Referring to FIG. 2 in conjunction with the structure shown in FIG. 1, an example set of traces 70 illustrates the fundamentals of the present approach. Ultrasonic scanning begins at $t_0$ as the transducer 12 of FIG. 1 moves at a scanning velocity (Vs) with respect to the surface 13. Measurement is periodically conducted as indicated by steps 71 of trace 72. That is, when measurement is to be conducted, step 71 (on/binary 1) is active.

Also at $t_0$, a sonic pulse 54 is provided via the pulsed output signal (trace 50) from the actuator power supply 32. As indicated by trace 74, each sonic pulse 54 causes a vertical displacement 75 to occur in the transducer 12 with respect to the surface 13 of FIG. 1. Arrow $P_{MAX}$ indicates the contact force at the maximum extent of the vertical displacement 75, which occurs at $t_1$. To ensure that $P_{MAX}$ is achieved, the timing circuit 26 of FIG. 1 counts through a calibrated interval 77 of a clock cycle 76. This interval 77 may be determined offline using knowledge of the transducer 12, the actuator 11, the dry couplant 20, and the sample 14, and therefore may be expected to vary with the particular design and materials used in the system 10.

At $t_1$, i.e., during the maximum vertical displacement 75 and thus concurrently with the sonic pulse 54, the ultrasonic pulser/receiver 30 of FIG. 1 generates ultrasonic waves 16 as the ultrasonic input pulse 27. The ultrasonic input pulse 27 (for measurement purposes) lasts until $t_2$, and thus is relatively non-existent when the sonic pulse 54 ends at $t_3$. Concurrently with the input pulse 27, the ultrasonic pulser/receiver 30 receives the ultrasonic return pulse 127 and relays this information to the host machine 22 of FIG. 1, wherein the digitizer 24 converts this value into a form that is readily usable in any subsequent control action/reporting of the scanning results. The entire sequence repeats beginning at $t_4$ and continuing through to $t_7$ at a sonic frequency.

Timing Approach

The actual contact time between the transducer 12 and the surface 13 of the structural sample 14 shown in FIG. 1 depends on the velocity of propagation of the ultrasonic waves 16, and also on the thickness (T) of the sample 14 and a thickness of the dry couplant 20. Thus, inspection of an aircraft fuselage skin, for instance, should require less contact time than that required for inspection of a thicker sample. Additionally, by lowering the sonic frequency, relatively large areas may be rapidly scanned at a reduced resolution. The sonic frequency may be increased up to the ultrasonic frequency for higher resolution inspections without departing from the intended inventive scope.

Close regulation of the momentary touching of the transducer 12 ensures that consistent hand or mechanical pressure is not required to establish constant contact with the surface 13. The timing circuit 26 synchronizes the timing of any intermittent contact between the actuator 11 and the surface 13 with the transmission and detection of the ultrasonic waves 16 from the transducer 12. This in turn ensures that efficient and consistent energy coupling is obtained without the use of wet couplant such as water or gel between the dry couplant 20 and the surface 13.

The actual measurement time ($t_m$) may be defined as follows:

$$t_m = \frac{2(T_{sample})}{v_{sample}} + \frac{2(T_{coupling\ medium})}{v_{coupling\ medium}} + \beta \quad (1)$$

where the values $T_{sample}$ and $T_{coupling}$ medium represent the thicknesses of the sample 14 and the dry couplant 20, respectively. The measurement is a pulse echo, and thus the distance traveled by the ultrasonic waves 16 is a factor of the two thicknesses $T_{sample}$ and $T_{coupling}$ medium. Ultrasonic wave velocity is a total velocity of the waves 16 through the sample 14, i.e., $v_{sample}$, and the dry couplant 20, i.e., $v_{coupling}$ medium. In equation (1), the factor, β represents the settling time required for stabilization of the contact pressure from a momentary touching.

A spatial sample interval time ($t_s$) may be defined as:

$$t_s = \frac{beam}{scan\ speed * \partial} \quad (2)$$

where the variable "scan speed" is provided by mechanical or hand movement, "beam" is the ultrasonic beam size or wavelength, and "∂" is a scalable factor that determines the final scanning resolution. The spatial sample interval time ($t_s$) is optimal when a ∂=1, and therefore, the inspection resolution is equivalent to the transducer beam size. The inspection resolution is not limited to the beam size with the present approach. Therefore, relatively large areas can be scanned rapidly if the resolution is less than 1, i.e., if ∂<1.

The contact duty cycle ($t_d$) may be defined below as:

$$t_d = \frac{measurement\ time}{spatial\ sample\ interval\ time} * 100\% \quad (3)$$

For example, a typical ultrasonic longitudinal velocity on a graphite epoxy composite having a fiber volume fraction of 60 percent would be approximately 0.138 inches/μsec. If the longitudinal velocity through the dry couplant 20 is assumed to be a factor of 5 or slower, then for a graphite epoxy composite thickness of 0.5 inches and coupling medium thickness of 0.25 inches, the wave propagation time would be 25.4 μseconds. Since ultrasonic measurement is rapid, the settling time, β, is an important factor in the control of the system 10. If the transducer tapping frequency can be adjusted to 1.0 kHz, then the total measurement time would be 0.0010254 seconds as determined using equation (1).

Depending on how the transducer 12 of FIG. 1 is controlled, the settling time could be much faster. Given a typical hand velocity of 2.4 inches/sec, a resolution factor ∂=0.5, and an ultrasonic beam diameter of 0.0625 inches, the spatial sample interval time ($t_s$) would be 0.052 seconds. This is the time available to perform the ultrasonic inspection at a given point during hand scanning, which is much more than the required measurement time.

Therefore, the measurement duty cycle is estimated as 1.97 percent. This indicates that the transducer 12 must be in contact with the surface 13 only 1.97 percent of the time. For a sample 14 having an inspection length of 12 inches, the ultrasonic inspection of which would take 5 seconds to complete, the transducer 12 would have to make 96 measurements, i.e., 96 momentary touches. The total required time the transducer must be in contact with the surface 13 in this particular example is 0.099 seconds, which is much less than the total measurement time of 5 seconds.

Figure 3:
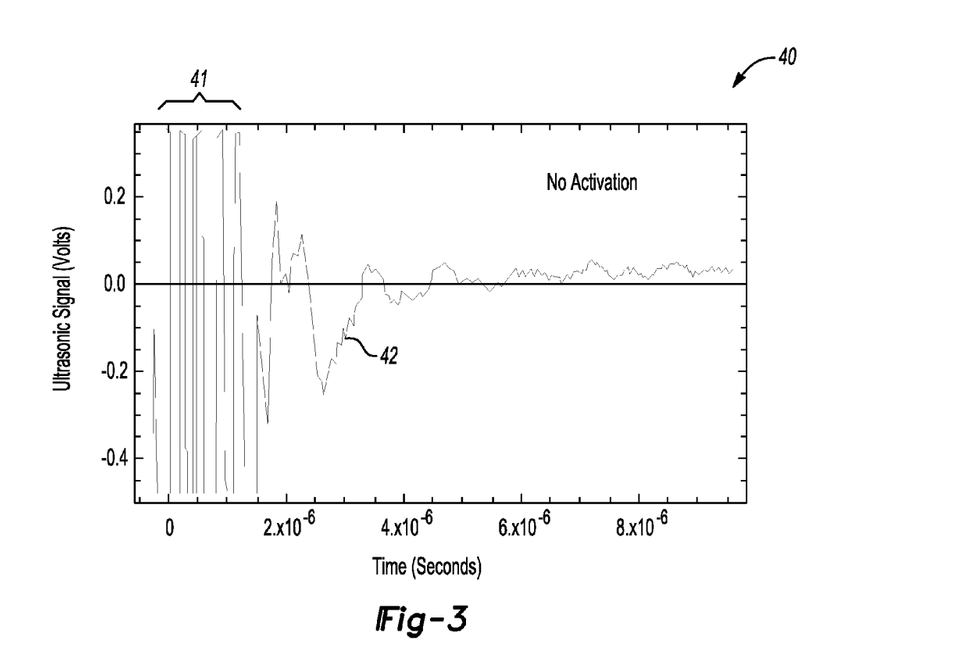
FIG. 3 is an example graph describing a baseline ultrasonic energy return (vertical axis) versus time (horizontal axis) in the system of FIG. 1A prior to activation of an actuator of the ultrasonic transducer.
Figure 4:
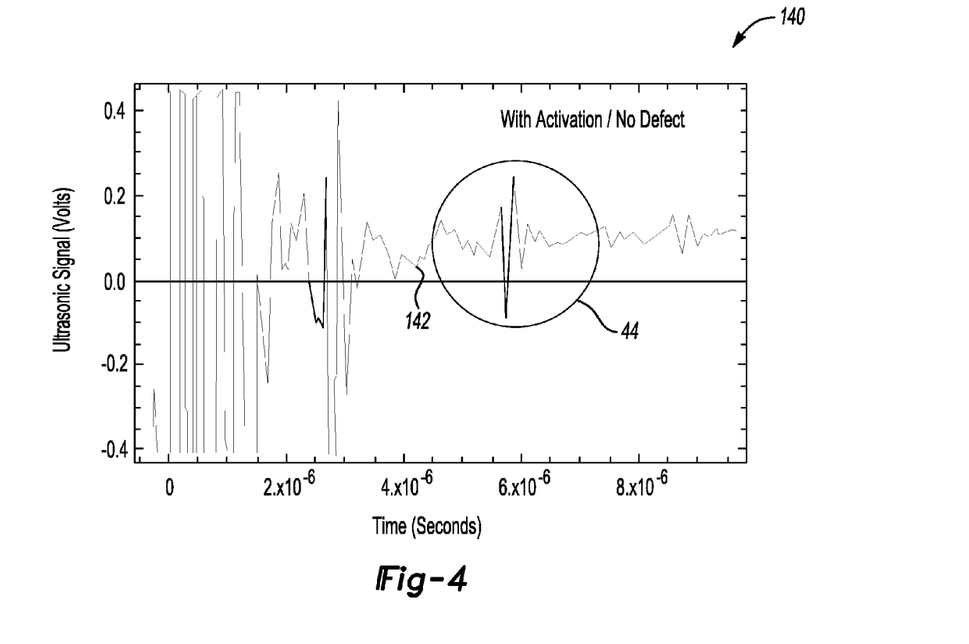
FIG. 4 is an example graph describing ultrasonic energy return versus time in the system of FIG. 1 in the absence of sample defects.
Figure 5:
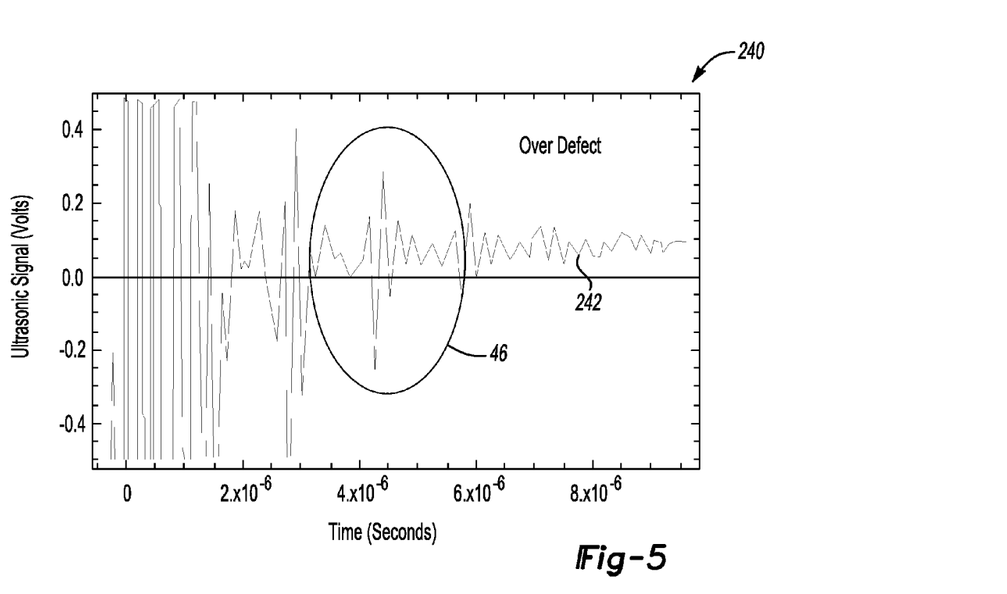
FIG. 5 is an example graph describing ultrasonic energy return versus time in the system of FIG. 1 in the presence of defects in the sample.

FIGS. 3-5 describe various example measurement results that are possible using the ultrasonic inspection system 10 of FIG. 1. FIG. 3 shows an example return waveform 40 when the actuator 11 of FIG. 1 is not activated and little to no ultrasonic energy is transmitted to the sample 14.

In FIG. 4, when the actuator 11 of FIG. 1 is activated and a surface 13 having no defects is ultrasonically measured, a return waveform 140 having a baseline back wall echo (region 44) is present in the return signal (trace 142). A variance from the baseline response of FIG. 4 may be used by the host machine 22 of FIG. 1 to detect a defect in the sample 14. For instance, FIG. 5 shows the measurement results as a return waveform 240 that may occur when an example defect is measured. A defect pattern (trace 46) may be detected in the return signal (trace 242). Such defects may be unknown, thus necessitating further analysis, or they may have a pattern or profile that can be matched to known defects.

Figure 6:
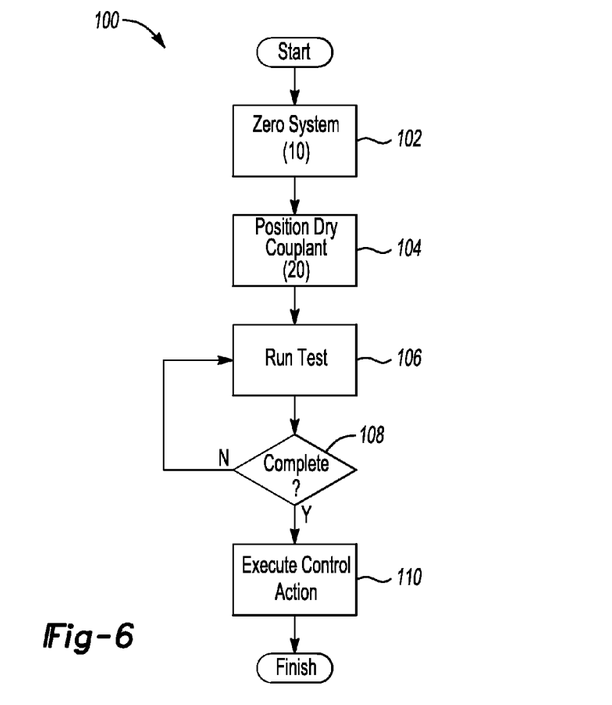
FIG. 6 is a flow chart describing an example method for inspecting a structural sample using the system of FIG. 1.

Referring to FIG. 6, an example inspection method 100 is described with reference to the ultrasonic inspection system 10 of FIG. 1. Beginning with step 102, the measurement system 18 is zeroed, a step that may include clearing all prior inspection data from memory of the host machine 22. Once zeroed, the method 100 proceeds to step 104.

At step 104, the transducer 12 may be positioned via the positioning device 33 with respect to the surface 13. Step 104 may also include positioning the dry couplant 20 between the transducer 12 and the surface 13, a step which may entail wrapping the transducer 12 in the dry couplant 20 or draping the dry couplant 20 over the surface 13.

At step 106, the transducer 12 of FIG. 1 is caused to vibrate at a calibrated ultrasonic frequency via the ultrasonic pulses (arrow 27 of FIG. 1) while the transducer 12 moves at scanning velocity Vs along the surface 13. Step 106 may include generation of the pulsed output signal (arrow 50) by the actuator power supply 32. The actuator 11 receives the pulsed output signal (arrow 50) and generates the train of sonic pulses 54 (see FIG. 2) which causes vertical displacement of the transducer 12 with respect to the plane of the surface 13, and a resultant exertion of a periodic force on the surface 13.

Also at step 106, motion of the transducer 12 is fully synchronized via the timing circuit 26 with any transmission of the ultrasonic waves 16 into the sample 14. As a result, data acquisition by the host machine 22 of FIG. 1 is synchronized with motion of the transducer 12 as the transducer 12 "floats" with respect to the surface 13 and intermittently touches the surface 13. Any back pulses from the ultrasonic waves 16 are read by the ultrasonic pulser/receiver 30 and recorded in memory 36 of the host machine 22 for subsequent diagnostic use and/or other control actions.

At step 108, the measurement system 18 of FIG. 1 next determines whether the inspection process has terminated. Step 108 may include detecting a signal from the user, or it may include monitoring the response to transmitted ultrasonic energy using the pulser/receiver 30. Steps 106 and 108 may be repeated in a loop until conditions change to indicate that the testing is complete. Once the inspection process has terminated the method 100 proceeds to step 110.

At step 110, the host machine 22 of FIG. 1 executes a suitable control action. Step 110 may entail, for instance, recording a passing or failing result in memory of the host machine 22 and/or repeating the inspection to verify the results. Step 110 may entail comparing the level of attenuation of ultrasonic waves 16 in the sample 14 to a calibrated set of waveforms recorded in memory device 36 of the host machine 22. With respect to the structural sample 14, step 110 may also entail withdrawing the sample 14 from further use, e.g., grounding an aircraft or spacecraft having the structural sample 14 in the form of a fuselage skin or composite layer as noted above. Other control actions may be envisioned as part of step 110.

By regulating the momentary touching of the transducer 12 using mechanical, electrical, magnetic, hydraulic, and/or other means, consistent hand pressure is not required for scanning. Timing of contact pressure is synchronized with the transmission and detection of the ultrasonic waves 16.

While the best modes for carrying out the invention have been described in detail, those familiar with the art to which this invention relates will recognize various alternative designs and embodiments for practicing the invention within the scope of the appended claims.

The invention claimed is:

1. A method for inspecting a structural sample using ultrasonic energy, the method comprising:
   positioning an ultrasonic transducer adjacent to a surface of the sample;
   transmitting ultrasonic energy into the sample using an ultrasonic transducer;
   applying force pulses to the transducer, concurrently with the transmission of the ultrasonic energy and at a frequency that is lower than a frequency of the ultrasonic energy, to thereby vertically displace the transducer and cause the transducer to exert a periodic force on the surface;
   moving the transducer with respect to the surface and in synchronization between the transmission of pulses with the periodic force and movement of the transducer;
   processing an ultrasonic return pulse from an ultrasonic pulser/receiver using a host machine to thereby quantify a level of attenuation of the ultrasonic input pulses within the sample; and
   using the host machine to detect a defect in the sample using the quantified level of attenuation;
   wherein an actuator and the transducer are enclosed within a housing having a perforated skirt; and
   applying a vacuum to the surface through pores in the perforated skirt while moving the transducer with respect to the surface.

2. The method of claim 1, wherein the frequency of the force pulses is a sonic frequency.

3. The method of claim 1, further comprising:
   positioning a dry couplant between an ultrasonic transducer and the surface of the sample.

4. The method of claim 3, wherein the dry couplant is an elastomer that encapsulates the transducer within a volume of fluid or layer of gel couplant.

5. The method of claim 1, wherein using a host machine to detect a defect in the structural sample includes comparing the level of attenuation to a calibrated set of waveforms recorded in a tangible, non-transitory memory device of the host machine.

6. The method of claim 1, wherein an actuator is connected to an actuator power supply, the method further comprising:
   modifying a contact duty cycle of the actuator power supply via the host machine and timing electronics to thereby optimize the contact time.

7. A system for inspecting a structural sample using ultrasonic energy, the system comprising:
   an actuator;
   an ultrasonic transducer connected to the actuator;
   a dry couplant positioned between the ultrasonic transducer and a surface of the structural sample;
   a scanning device that moves the actuator and the transducer with respect to the surface during inspection of the sample,
   a scanning device that is synchronized to the transmission of the ultrasonic energy with the force pulses and with the transducer movement with respect to the surface; and
   a measurement system in communication with the ultrasonic transducer that includes a pulsed actuator power supply, an ultrasonic pulser/receiver, and a host machine having a processor and tangible, non-transitory memory on which is recorded a set of instructions for inspecting the sample, wherein execution of the instructions by the processor causes:
   the ultrasonic pulse/receiver to transmit ultrasonic energy into the sample via the transducer;
   the pulsed actuator power supply to cause the actuator to apply force pulses to the transducer concurrently with the transmission of the ultrasonic energy and movement of the transducer and actuator, wherein the force pulses vertically displace the transducer and cause the transducer to exert a periodic force on the surface;
   the processor to process ultrasonic return pulses from the ultrasonic pulser/receiver to thereby quantify a level of attenuation of the energy within the sample;
   the host machine to detect a defect in the sample using the quantified level of attenuation and host machine to detect the location of the measurement that indicates the defect in the sample; and
   a housing in fluid communication with a vacuum source, wherein the actuator and the transducer are enclosed in the housing.

8. The system of claim 7, wherein the force pulses are transmitted at a sonic frequency.

9. The system of claim 7, wherein the actuator is one of a piezoelectric stack and a linear voice coil motor.

10. The system of claim 7, wherein the housing includes a perforated skirt that contacts the surface and defines a plurality of pores in fluid communication with the vacuum source.

11. The system of claim 7, wherein the dry couplant encapsulates the transducer within a volume of liquid or gel couplant.

12. A method for inspecting a structural sample using ultrasonic energy, the method comprising:
   positioning a dry couplant in the form of a flexible membrane between an ultrasonic transducer and a surface of the sample;
   using an actuator to vertically displace the transducer and thereby cause the transducer to exert periodic force pulses on the surface of the structural sample, wherein the periodic force has a sonic frequency of at least 50 Hz;
   transmitting ultrasonic energy at an ultrasonic frequency of at least 1 MHz into the structural sample using the transducer and an ultrasonic pulser/receiver;
   synchronizing the transmission of the ultrasonic energy with the force pulses and the transducer movement with respect to the surface;

quantifying a level of attenuation of the ultrasonic input pulses within the sample, including processing ultrasonic return pulses from the sample using a host machine; and using the host machine to detect a defect in the sample as a function of the level of attenuation and host machine to detect the location of the measurement that indicates the defect in the sample;

enclosing the transducer in a housing having a perforated skirt; and applying a vacuum to the surface via pores defined by the perforated skirt.

13. The method of claim 12, wherein the periodic force pulses have a sonic frequency of between 60 Hz and 70 Hz, and wherein the ultrasonic frequency is at least 30 MHz.

14. The method of claim 12, wherein using an actuator to cause the transducer to exert periodic force pulses includes using one of a piezoelectric stack and a linear voice cod motor.

15. The method of claim 12, further comprising positioning a wet fluid or gel couplant between the transducer and the dry couplant.

16. The method of claim 15, further comprising:
encapsulating the transducer in a volume of fluid or gel, wherein the wet fluid or gel is the couplant.

17. The method of claim 12, wherein synchronizing the transmission of the ultrasonic energy with the force pulses includes calculating an actual measurement time ($t_m$) defined as:

$$t_m = \frac{2(T_{sample})}{v_{sample}} + \frac{2(T_{coupling\ medium})}{v_{coupling\ medium}} + \beta$$

where and $T_{sample}$ and $T_{coupling\ medium}$ respectively represent the thicknesses of the sample and the dry couplant, $v_{sample}$ and $v_{coupling\ medium}$ represent the total velocity through the sample and the dry couplant, respectively, of waves of the ultrasonic energy, and $\beta$ is the settling time required for stabilization of contact pressure from one of the periodic force pulses.

* * * * *